US010901978B2

(12) United States Patent
Xu et al.

(10) Patent No.: US 10,901,978 B2
(45) Date of Patent: Jan. 26, 2021

(54) SYSTEM AND METHOD FOR CORRELATION OF PATHOLOGY REPORTS AND RADIOLOGY REPORTS

(71) Applicant: KONINKLIJKE PHILIPS N.V., Eindhoven (NL)

(72) Inventors: Ye Xu, Milford, CT (US); Yuechen Qian, Briarcliff Manor, NY (US)

(73) Assignee: Koninklijke Philips N.V., Eindhoven (NL)

( * ) Notice: Subject to any disclaimer, the term of this patent is extended or adjusted under 35 U.S.C. 154(b) by 1281 days.

(21) Appl. No.: 15/035,772

(22) PCT Filed: Nov. 14, 2014

(86) PCT No.: PCT/IB2014/066034
§ 371 (c)(1),
(2) Date: May 11, 2016

(87) PCT Pub. No.: WO2015/079353
PCT Pub. Date: Jun. 4, 2015

(65) Prior Publication Data
US 2016/0267226 A1  Sep. 15, 2016

Related U.S. Application Data

(60) Provisional application No. 61/908,932, filed on Nov. 26, 2013.

(51) Int. Cl.
*G06F 16/23* (2019.01)
*G16H 15/00* (2018.01)
(Continued)

(52) U.S. Cl.
CPC .......... *G06F 16/2365* (2019.01); *G06F 19/00* (2013.01); *G16H 10/60* (2018.01); *G16H 15/00* (2018.01); *G16H 40/20* (2018.01)

(58) Field of Classification Search
CPC ................................................. G06Q 50/22–24
See application file for complete search history.

(56) References Cited

U.S. PATENT DOCUMENTS 7,936,908 B2  5/2011  Brackett
8,244,684 B2  8/2012  Ando et al.
(Continued)

FOREIGN PATENT DOCUMENTS

CN     1983258 A      6/2007
WO     2013028762 A1  2/2013

OTHER PUBLICATIONS

El Saadawi, G.M., Tseytlin, E., Legowski, E. et al. "A natural language intelligent tutoring system for training pathologists: implementation and evaluation." Adv in Health Sci Educ 13, 709-722 (2008). https://doi.org/10.1007/s10459-007-9081-3 (Year: 2008).*

*Primary Examiner* — Robert A Sorey (57) ABSTRACT

A system for correlating patient radiology and pathology reports to track discordance among radiology and pathology diagnoses includes a natural language processor engine which extracts radiological information and pathology information. A correlation module correlates the radiology information and pathology information in a specific time period. A visualization graphical user interface indicates the correlation of radiology information and pathology information in a patient history. A tracking module which tracks misdiagnosis cases.

22 Claims, 8 Drawing Sheets (51) Int. Cl.
*G16H 40/20* (2018.01)
*G16H 10/60* (2018.01)
*G06F 19/00* (2018.01)

(56) References Cited

U.S. PATENT DOCUMENTS

| | | |
|---|---|---|
| 8,793,143 B2 | 7/2014 | Makino et al. |
| 2004/0225531 A1 | 11/2004 | Serrano et al. |
| 2006/0161456 A1* | 7/2006 | Baker .................. G06F 19/00 705/2 |
| 2007/0067185 A1* | 3/2007 | Halsted ................ G16H 50/20 705/2 |
| 2008/0046286 A1 | 2/2008 | Halsted |
| 2011/0276346 A1 | 11/2011 | Reiner |
| 2012/0208161 A1* | 8/2012 | Takata .................. G16H 40/20 434/262 |
| 2012/0221347 A1 | 8/2012 | Reiner |
| 2013/0030305 A1* | 1/2013 | Yu ........................ A61B 5/0084 600/476 |
| 2013/0346095 A1 | 12/2013 | Buckland et al. |
| 2014/0006926 A1 | 1/2014 | Yeluri et al. |
| 2018/0060487 A1* | 3/2018 | Barkan ................ G16H 70/60 |

* cited by examiner

SYSTEM AND METHOD FOR CORRELATION OF PATHOLOGY REPORTS AND RADIOLOGY REPORTS

CROSS-REFERENCE TO PRIOR APPLICATIONS

This application is the U.S. National Phase application under 35 U.S.C. § 371 of International Application No. PCT/IB2014/066034, filed on Nov. 14, 2014, which claims the benefit of U.S. Provisional Application No. 61/908,932, filed on Nov. 26, 2013. These applications are hereby incorporated by reference herein.

The present application relates generally to correlating pathology and radiology reports. It finds particular application in conjunction with promptly presenting graphical information to a user from which the user can view agreement or disagreement between radiology and pathology report findings and will be described with particular reference thereto. However, it is to be understood that it also finds application in other usage scenarios and is not necessarily limited to the aforementioned application.

After examining a patient and the patient's clinical history, radiologists must often make educated inferences about a patient's condition. To verify a diagnosis, patients are often referred to other doctors for pathology or surgical exams. Once the patient has gone to these exams, radiologists and hospital administrators often want more information regarding the accuracy of the radiologist's initial inference, however with more detailed, and enriched histories it has become more difficult for radiologists and administrators to quickly capture a detailed view of a patient's medical history. Further, once a complete patient medical history is formed, it is difficult to compare a single patient medical history to a database of patient medical histories to determine how many radiology reports were concordant or discordant with their corresponding pathology reports. Mapping this information is time consuming but without sufficient correlation, it is difficult to determine in which kinds of situations a misdiagnosis occurred, what led to the misdiagnosis, and whether the hospital's misdiagnosis rate follows an accepted standard so radiologists can adjust their workflow later.

More and more radiologists have envisioned that the next frontier in the improvement of radiology workflow is not in the enhancement of hanging protocol, a faster processor or an improved graphical user interface. On the contrary, they envisioned that the next frontier is an intelligent way to show complex information graphically and provide information to radiologists promptly. For example, radiologists need to have a cross-section between radiology and pathology worlds and see how many radiology reports were concordant or discordant with the pathology reports.

Figure 1:
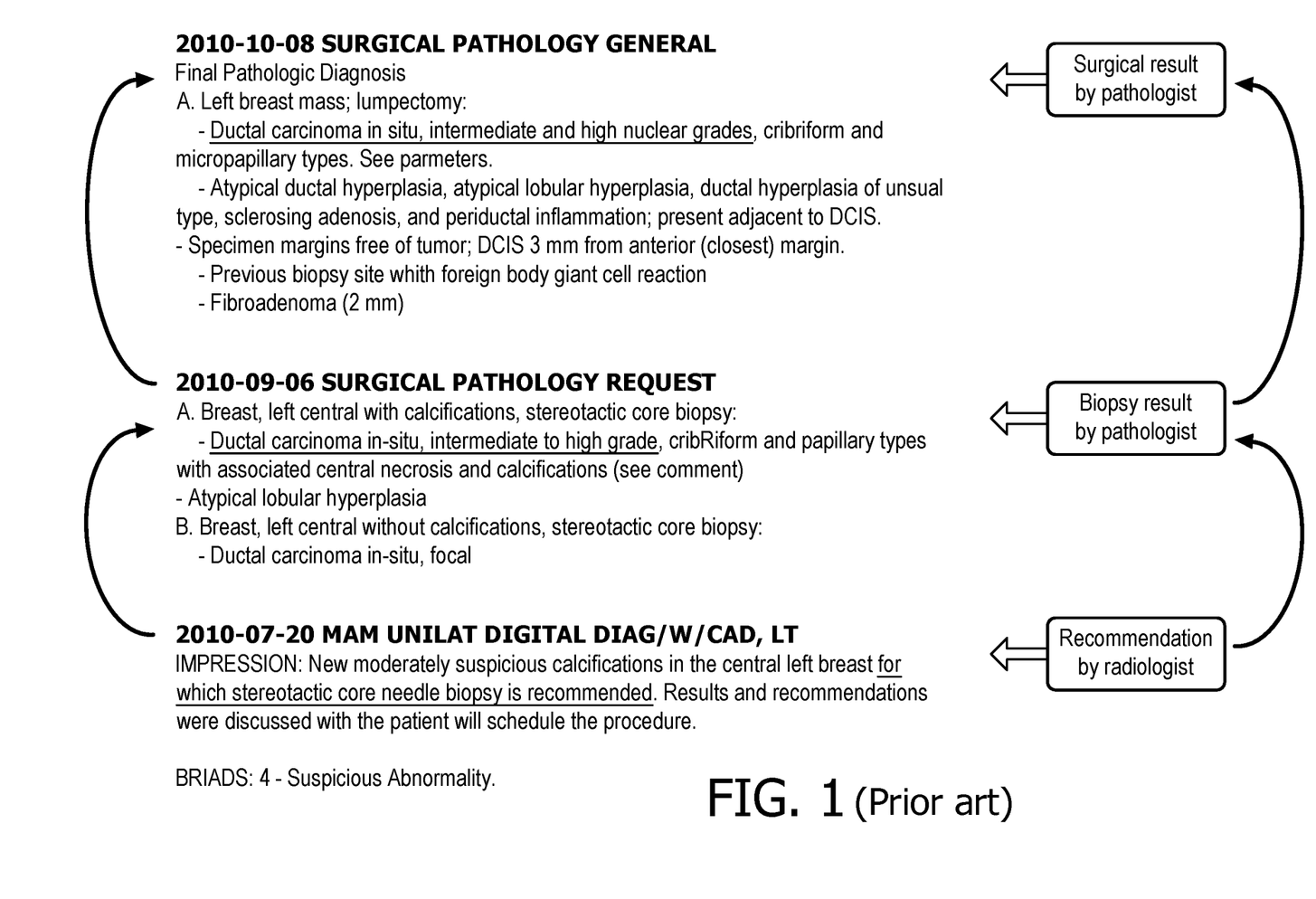
FIG. 1 illustrates a correlation workflow of a radiology report, a biopsy, and a surgical result according to aspects of the present application.

For example, in FIG. 1, a female patient was found with a suspicious calcification in her central left breast on Jul. 20, 2010 (for example) and was suggested for a biopsy on the same day. Almost one and a half months later, a biopsy was done, and was diagnosed with "Ductal carcinoma in-situ", which is a cancer. Another month later, she got a lumpectomy, and the final surgical result also confirmed its malignancy. Radiologists need a tool to promptly correlate this information to avoid wasting time searching for such information. Other clinicians like oncologists and general practitioners may have the similar needs.

Further, healthcare providers, such as administrators and the chief of radiology department need a quality control system to monitor healthcare quality. But, with the enriched patients' histories, they have difficulties to have a clear view of them. For example, they want to know radiologists' performance of diagnosis by correlating pathology results with radiologists' interpreting diagnosis results and find their discordance rate. It is desirable to have an intelligent way to show this complex information graphically. A need exists for a tool which not only provides additional clinical insight, but also enhances radiologists' productivity.

The present application provides a system and method to track discordance cases and get insight from correlation of pathology reports and radiology reports. The present application also provides new and improved methods and systems which overcome the above-referenced problems and others.

In accordance with one aspect, a system for correlating patient radiology and pathology reports to track discordance among radiology and pathology diagnoses is provided. The system includes a natural language processor engine which extracts radiological information and pathology information. A correlation module correlates the radiology information and pathology information in a specific time period according to guidelines and/or the needs of the user. A visualization graphical user interface indicates the correlation of radiology information and pathology information in a patient history. A tracking module monitors correlation data, compute diagnostic performance, and track misdiagnosis cases.

In accordance with another aspect, a method for correlating patient radiology and pathology reports is provided. The method including extracting radiological information and pathology information, correlating the radiology information and pathology information in a specific time period; indicating the correlation of radiology information and pathology information in a patient history, and monitoring correlation data to compute diagnostic performance and track misdiagnosis cases.

In accordance with another aspect, a system for correlating patient radiology and pathology reports is provided. The system including one or more processor programmed to extract radiological information and pathology information, correlate the radiology information and pathology information in a specific time period, indicate the correlation of radiology information and pathology information in a patient history, and monitor correlation data to compute diagnostic performance and track misdiagnosis cases.

One advantage resides in the reduction in time spent by radiologists or other medical professional in generating a thorough clinical history for a patient.

Another advantage resides in graphically correlating and comparing radiology interpretations with pathology findings.

Another advantage resides in tracking discordance patient cases.

Another advantage resides in improved clinical workflow.

Another advantage resides in improved patient care.

Still further advantages of the present invention will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

The present application is directed to evaluate diagnostic accuracy of radiologists with the help of the automatic correlation of pathology reports and radiology reports. Radiologists and hospital administrators are able to monitor patient care and health care quality through a graphical diagnostic analysis of positive and negative diagnostic findings. The present application utilizes this analysis by extracting radiological diagnosis and pathology outcomes, correlating the radiology studies of the radiologists with the pathology reports based upon a specific time period according to guidelines, visually organizing the information in a user interface, and offering tracking information to monitor the trend of data and misdiagnosis.

Figure 2:
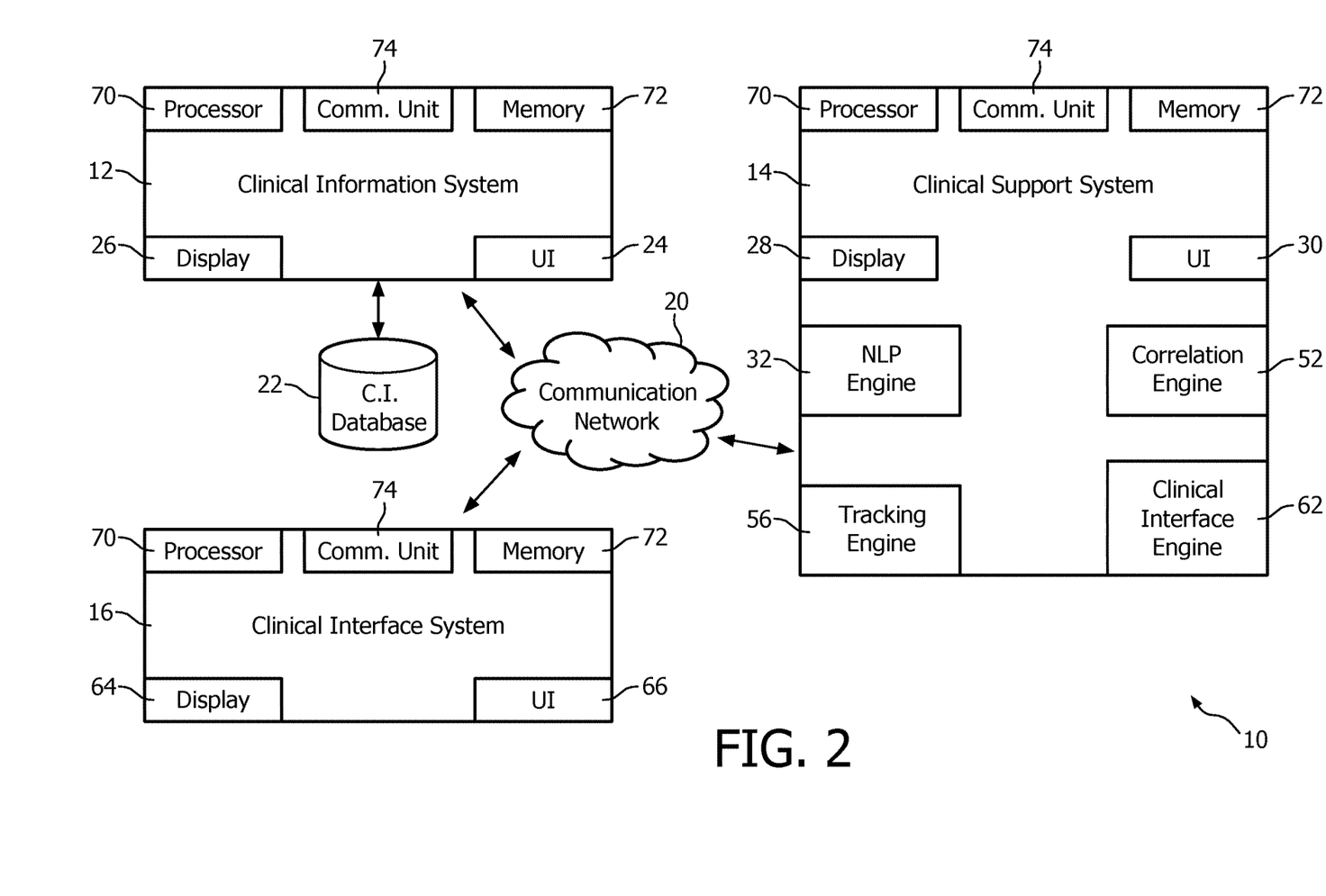
FIG. 2 illustrates a block diagram of an IT infrastructure of a medical institution according to aspects of the present application.

With reference to FIG. 2, a block diagram illustrates one embodiment of an IT infrastructure 10 of a medical institution, such as a hospital. The IT infrastructure 10 suitably includes a clinical information system 12, a clinical support system 14, clinical interface system 16, and the like, interconnected via a communications network 20. It is contemplated that the communications network 20 includes one or more of the Internet, Intranet, a local area network, a wide area network, a wireless network, a wired network, a cellular network, a data bus, and the like. It should also be appreciated that the components of the IT infrastructure be located at a central location or at multiple remote locations.

The clinical information system 12 stores clinical documents including radiology reports, pathology reports, lab reports, and the like in a clinical information database 22. A clinical document may comprise documents with information relating to an entity, such as a patient. Some of the clinical documents may be free-text documents, whereas other documents may be structured document. Such a structured document may be a document which is generated by a computer program, based on data the user has provided by filling in an electronic form. For example, the structured document may be an XML document. Structured documents may comprise free-text portions. Such a free-text portion may be regarded as a free-text document encapsulated within a structured document. Consequently, free-text portions of structured documents may be treated by the system as free-text documents. Each of the clinical documents contains a list of information items. The list of information items including strings of free text, such as phases, sentences, paragraphs, words, and the like. The information items of the clinical documents can be generated automatically and/or manually. For example, various clinical systems automatically generate information items from previous clinical documents, dictation of speech, and the like. As to the latter, user input devices 24 can be employed. In some embodiments, the clinical information system 12 include display devices 26 providing users a user interface within which to manually enter the information items and/or for displaying clinical documents. In one embodiment, the clinical documents are stored locally in the clinical information database 22. In another embodiment, the clinical documents are stored in nationally or regionally in the clinical information database 22. Examples of patient information systems include, but are not limited to, electronic medical record systems, departmental systems, and the like.

Figure 3:
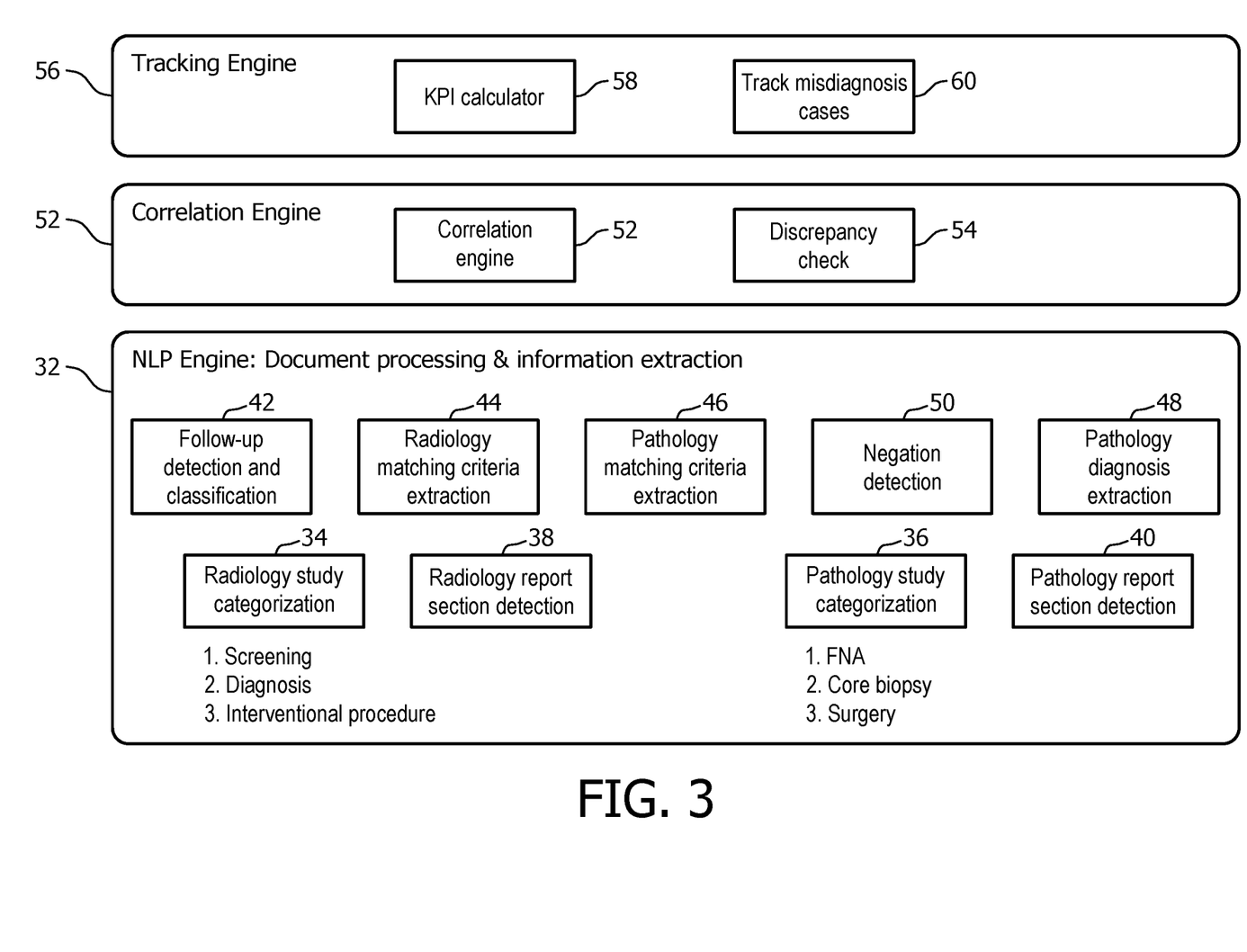
FIG. 3 illustrates a flowchart diagram of the operation of a clinical support system according to aspects of the present application.

With reference to FIGS. 2 and 3, the clinical support system 14 processes the clinical documents to detect information items in the clinical documents and to detect a pre-defined list of pertinent clinical findings and information. The clinical support system 14 further characterizes the clinical documents by their corresponding document type and extracts information items from the clinical documents which relate to the various headings of the clinical documents. After extraction of the information items, the clinical support system 14 determines whether a current clinical document suggests any follow-up procedure, such as biopsy, follow-up imaging, lab test, surgery, etc. and extracts information items relating to a diagnosis in a pathology report. The clinical support system 14 also correlates clinical documents that include matching criteria which are then utilized to generate a user interface that allows the user to view the correlation among radiology studies and pathology reports. The clinical support system 14 includes a display 28 such as a CRT display, a liquid crystal display, a light emitting diode display, to display the information items and user interface and a user input device 30 such as a keyboard and a mouse, for the clinician to input and/or modify the provided information items.

Specifically, the clinical support system 14 includes a natural language processing engine 32 which processes the clinical documents to detect information items in the clinical documents and to detect a pre-defined list of pertinent clinical findings and information. To accomplish this, the natural language processing engine 32 segments the clinical documents into information items including sections, paragraphs, sentences, and the like. Typically, clinical documents contain a time-stamped header with protocol information in addition to clinical history, techniques, comparison, findings, impression section headers, and the like. The content of sections can be easily detected using a predefined list of section headers and text matching techniques. Alternatively, third party software methods can be used, such as MedLEE. For example, if a list of pre-defined terms is given, string matching techniques can be used to detect if one of the terms is present in a given information item. The string matching techniques can be further enhanced to account for morphological and lexical variant and for terms that are spread over the information item. If the pre-defined list of terms contains ontology IDs, concept extraction methods can be used to extract concepts from a given information item. The IDs refer to concepts in a background ontology, such as SNOMED or RadLex. For concept extraction, third-party solutions can be leveraged, such as MetaMap. Further, natural language processing techniques are known in the art per se. It is possible to apply techniques such as template matching, and identification of instances of concepts, that are defined in ontologies, and relations between the instances of the concepts, to build a network of instances of semantic concepts and their relationships, as expressed by the free text.

The natural language processor engine 32 also characterizes the clinical documents by their corresponding document type. By analyzing the pertinent clinical information, the natural language processor engine 32 determines whether the clinical documents and information items relate to a radiology study or pathology report. For example, a list of pre-defined terms for each type of document is utilized by the natural language processor engine 32 to detect if one or more of the terms is present in a radiology study or pathology report. The natural language processor engine 32 also differentiates between the various study types. Specifically, the natural language processor engine 32 includes a radiology study categorization engine 34 and a pathology report categorization engine 36. The natural language processor engine 32 utilizes the radiology study categorization engine 34 to determine the various study types included within a radiology study. For example, radiology study categorization engine 34 determines whether the current radiology study is a screening exam, a diagnosis exam or an interventional (imaging-guided biopsy) procedure, etc. Similarly, the pathology report categorization engine 36 determines the various study types included in a pathology report. For example, the pathology report categorization engine 36 determines whether the current pathology report is a fine needle aspiration, core biopsy, surgery, etc. In one embodiment, the radiology study categorization engine 34 and the pathology report categorization engine 36 utilize a classifier with an input of extracted key words in a radiology report or a pathology report to determine the type of the study of radiology report or pathology report.

The natural language processor engine 32 also extracts information items from the clinical documents which relate to the various headings of the clinical documents. To accomplish this, the natural language processor engine 32 includes a radiology study section detection engine 38 and a pathology report section detection engine 40. The natural language processor engine 32 utilizes the radiology study section detection engine 38 to extract the various sections of a radiology study. For example, the radiology study section detection engine 38 extracts the clinical information, findings, impression, etc. section of a radiology study. Likewise, the natural language processor engine 32 utilizes the pathology report section detection engine 40 to extract the various section of a pathology report. For example, the pathology report section detection engine 40 extracts the clinical history, specimens received, final pathologic diagnosis, etc. sections from a pathology report. In one embodiment, the radiology study section detection engine 38 and the pathology report section detection engine 40 utilize a header matching algorithm to extract the various sections of the clinical documents. In another embodiment, the radiology study section detection engine 38 and the pathology report section detection engine 40 utilizes existing natural language processing algorithms like MedLEE or MetaMap to extract the clinical document sections. Additionally, the radiology study section detection engine 38 and the pathology report section detection engine 40 can utilize user-defined rules to extract certain types of sections that may appear in the document. In some cases, there may many header expressions for a one particular section. To account for this, the radiology study section detection engine 38 and the pathology report section detection engine 40 utilizes a list of header expressions in order to detect each section. For example, fragments of a report starting with "IMPRESSION", "IMPRESSIONS", "CONCLUSION", "CONCLUSIONS", "OPINION", "SUMMARY" are all instances of the impression section.

A follow-up detection and classification engine 42 of the natural language processor engine 32 determines whether a clinical document study suggests any follow-up procedure, such as biopsy, follow-up imaging, lab test, surgery, and the like. Specifically, the follow-up detection and classification engine 42 extracts the impression section in a radiology study, and utilizes regular expressions to find information items containing suggestion of follow-up procedure. For example, if a sentence in an impressions section of a radiology report in a mammogram study contains a key word, such as "biopsy", "fna", "surgical consultation", and "excision" and is followed by a key word, such as "recommend", "deliver", "consider", "correlate to", "suggest", "will be of choice", "could be performed", then the follow-up detection and classification engine 42 suggests a follow-up procedure.

The natural language processor engine 32 also matches information items of various clinical documents which match similar criteria. To accomplish this, the natural language processor engine 32 includes a radiology matching criteria extraction engine 44 and a pathology matching criteria extraction engine 46. Specifically, the radiology matching criteria extraction engine 44 and the pathology matching criteria extraction engine 46 determine whether information items in radiology studies and/or pathology reports refers to a similar criteria such as an anatomy location, follow-up procedure, result, and the like. For example, in a radiology study of a mammogram study, the radiology matching criteria extraction engine 44 and the pathology matching criteria extraction engine 46 extract laterality, o'clock and depth information of lesions in radiology reports and pathology reports. Multiple anatomy locations in the radiology study and pathology report will be considered. For example, if the impressions section of a radiology report suggested a biopsy in the left breast, but the right breast appeared normal then the pathology matching criteria extraction engine 46 correlates the left breast in a correlated pathology report and the radiology matching criteria extraction engine 44 correlates the left breast in a correlated radiology report, not right breast. To accomplish this, the radiology matching criteria extraction engine 44 and the pathology matching criteria extraction engine 46 utilizes a matching criteria extraction algorithm which includes list of correlated pre-defined terms. A string matching techniques can be then utilized used to detect if one of the terms is present in a given information item in the clinical documents.

A pathology diagnosis extraction engine 48 of the natural language processor engine 32 extracts information items relating to a diagnosis in a pathology report. Specifically, the pathology diagnosis extraction engine 48 detects the malignancy of a pathology result, such as "Ductal Carcinoma In Situ", which is malignant, and "Fibroadenoma", which is a benign pathology diagnosis result. In order to differentiate a pathology diagnosis result, the pathology diagnosis extraction engine 48 utilizes dictionary containing all known names of pathology results of benign and malignant diagnosis. For example, the pathology diagnosis extraction engine 48 extracts diagnosis from the pathology report and matches the diagnosis to a defined diagnosis to determine its malignancy of a pathology diagnosis result.

The natural language processor engine 32 further includes a negation detection engine 50 which tracks whether an information item contains a negative meaning. For example, "No abnormal enhancement in either breast, specifically no abnormal enhancement correlating to the biopsy proven DCIS in the central left breast" does not suggest a biopsy because it has "no" appearing in front of an information item pattern suggesting biopsy. The negation detection engine 50 can utilize regular expression patterns to detect whether the biopsy is a recommendation or not.

The clinical support system 14 also includes a correlation engine 52 which correlates clinical documents that include matching criteria to other clinical documents. Specifically, the correlation engine 52 correlates interpretations in one or more radiology studies with related pathology outcomes in one or more pathology reports. After extracting matching information items from a radiology report and a pathology report, the correlation engine 52 determines whether those two clinical documents are correlated, for example by matched anatomy location. The correlation engine 52 utilizes a Unified Medical Language System (UMLS), to determine if anatomy appearing in the clinical documents has the same SNOMED concept. For example, clinical documents which include the anatomy "vertebra" and "spine", "hepatic lesion" and "a liver mass" match because they have the same concept. In case of breast cancer studies, anatomy location information can include the laterality, depth and o'clock position of findings.

The correlation engine 52 also includes a discrepancy check engine 54 that checks correlated clinical documents for discrepancies in the results. For example, if there is a mismatch of radiology diagnosis results with pathology results, the discrepancy check engine 54 provides details describing the discrepancy. For example, for a breast patient, radiologists will compare a patient's BIRADS score that appears in a radiology reports to its pathology result. If there is a conflict between the radiology study diagnosis (such as BIRADS: 4, suspicious finding, positive finding) and pathology report result (for example, Fibroadenoma, a benign case, negative finding), the discrepancy check engine 54 documents the discrepant which is displayed to the user.

The clinical support system 14 also includes a tracking engine 56 that monitors the trend of diagnoses and tracks misdiagnosed cases. Specifically, the tracking engine 56 includes a key performance indicator (KPI) calculating engine 58 and a misdiagnosis case tracking engine 60. The KPI calculating engine 58 accumulates matching diagnosis within the clinical documents, and provides statistics regarding the performance of the diagnosis (calculate all KPI values). The KPI calculating engine 58 also generates a scorecard of all KPIs with the calculated values of KPIs with standard ranges accepted in each field. The scorecard will also track the calculated values of KPIs and other details for the misdiagnosed cases.

The misdiagnosis case tracking engine 60 tracks the clinical outcomes of radiologists, collectively (whole radiologists in a hospital) or individually (each radiologist) in a specific time period, for example, one year, or two years. The misdiagnosis case tracking engine 60 also utilizes a data structure to store information of each correlation, including its radiology report identification and pathology reports identification to assist in to tracking cases with misdiagnosis. Utilizing the data structure, the misdiagnosis case tracking engine 60 tracks the details of true positive (TP) and false positive (FP) cases and determines the reasons for the misdiagnosis by reading contents of clinical document, especially for FP cases. Specifically, the misdiagnosis case tracking engine 60 matches the clinical documents related to a FP cases and reports any details in the information items which do not match.

The clinical support system 14 also includes a clinical interface engine 62 that generates a user interface that allows the user to view the correlation among radiology studies and pathology reports. In one embodiment, the clinical interface engine 62 generates a user interface that displays the discrepancy and correlation of diagnosis within clinical documents. For example, the clinical interface engine 62 generates a visualization that includes rows that are highlighted that correspond to pathology reports and radiology reports that are correlated. In another embodiment, the visualization tool can be used in the routine clinical workflow by clinicians to review the patient history. For example, when the user selects a study in the user interface, the clinical interface engine 62 generates a display of the actual patient under investigation and visualizes reports with concordant/discordant results. In another embodiment, the clinical interface engine 62 generates a user interface including a scorecard with the calculated values of KPIs with standard ranges accepted in each field. For example, a yellow bar may indicates the optimal range for each KPI, and a cross marker in blue may indicates the real performance value in a hospital.

The clinical interface system 16 displays the user interface such that the user may view the correlation among radiology studies and pathology reports. The clinical interface system 16 receives the user interface and displays the view to the caregiver on a display 64. The clinical interface system 16 also includes a user input device 66 such as a touch screen or keyboard and a mouse, for the clinician to input and/or modify the user interface views. Examples of caregiver interface system include, but are not limited to, personal data assistant (PDA), cellular smartphones, personal computers, or the like.

The components of the IT infrastructure 10 suitably include processors 70 executing computer executable instructions embodying the foregoing functionality, where the computer executable instructions are stored on memories 72 associated with the processors 70. It is, however, contemplated that at least some of the foregoing functionality can be implemented in hardware without the use of processors. For example, analog circuitry can be employed. Further, the components of the IT infrastructure 10 include communication units 74 providing the processors 70 an interface from which to communicate over the communications network 20. Even more, although the foregoing components of the IT infrastructure 10 were discretely described, it is to be appreciated that the components can be combined.

Figure 4:
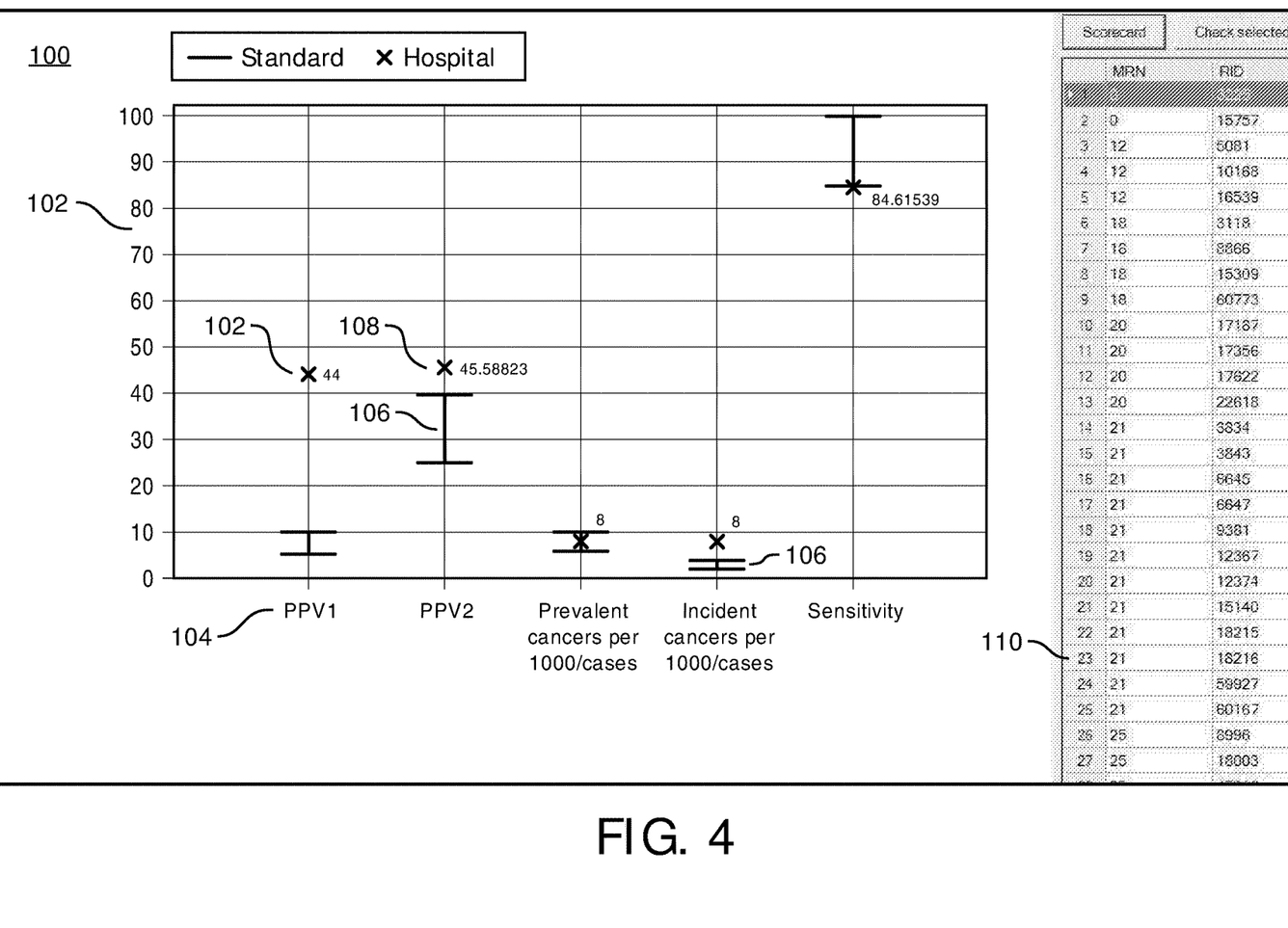
FIG. 4 illustrates an exemplary embodiment of scorecard visualization generated by clinical support system according to aspects of the present application.

With reference to FIG. 4, an exemplary embodiment of a scorecard visualization 100 generated by clinical support system is illustrated. The scorecard visualization 100 displays statistics with KPIs and their accepted ranges for each field. The scorecard visualization 100 includes a vertical axis representing the KPI value 102 and a horizontal axis representing the various types of misdiagnosed cases. The scorecard visualization includes an optimal range for each KPI 106 and the real performance value of a specific medical institution 108. For example, the standard accepted value for positive predictive value (PPV2) is in the range of 25%-40%, while its real performance value in the medical institution is around 45.58%. The scorecard visualization 100 also enables the user to click on each KPI value to track details of the misdiagnosed cases 110.

Figure 5:
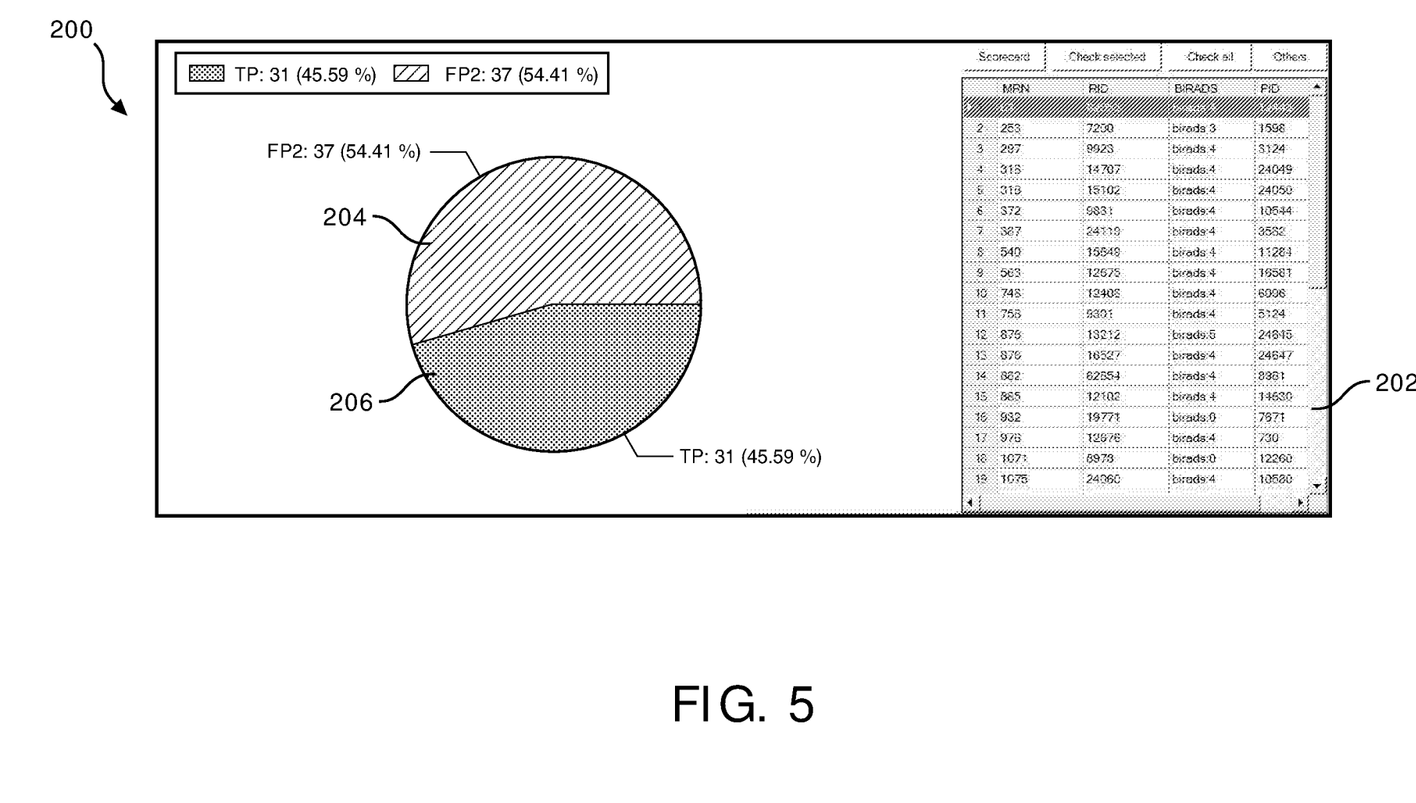
FIG. 5 illustrates an exemplary embodiment of a user interface generated by the clinical support system according to aspects of the present application.

With reference to FIG. 5, an exemplary embodiment of a user interface 200 generated by the clinical support system is illustrated. The user interface 200 tracks the clinical outcome of various radiologists. Specifically, the user interface 200 enables the user to select a particular study and track the outcome of that study. The user interface 200 includes a visualization that includes the respective percentages of true positives 202 and false positives 204. The user interface 200 also enables the user to track down details of true positive and false positive cases as well as display the respect clinical documents 206 such that the user can read and determine the reasons for misdiagnosis.

Figure 6:
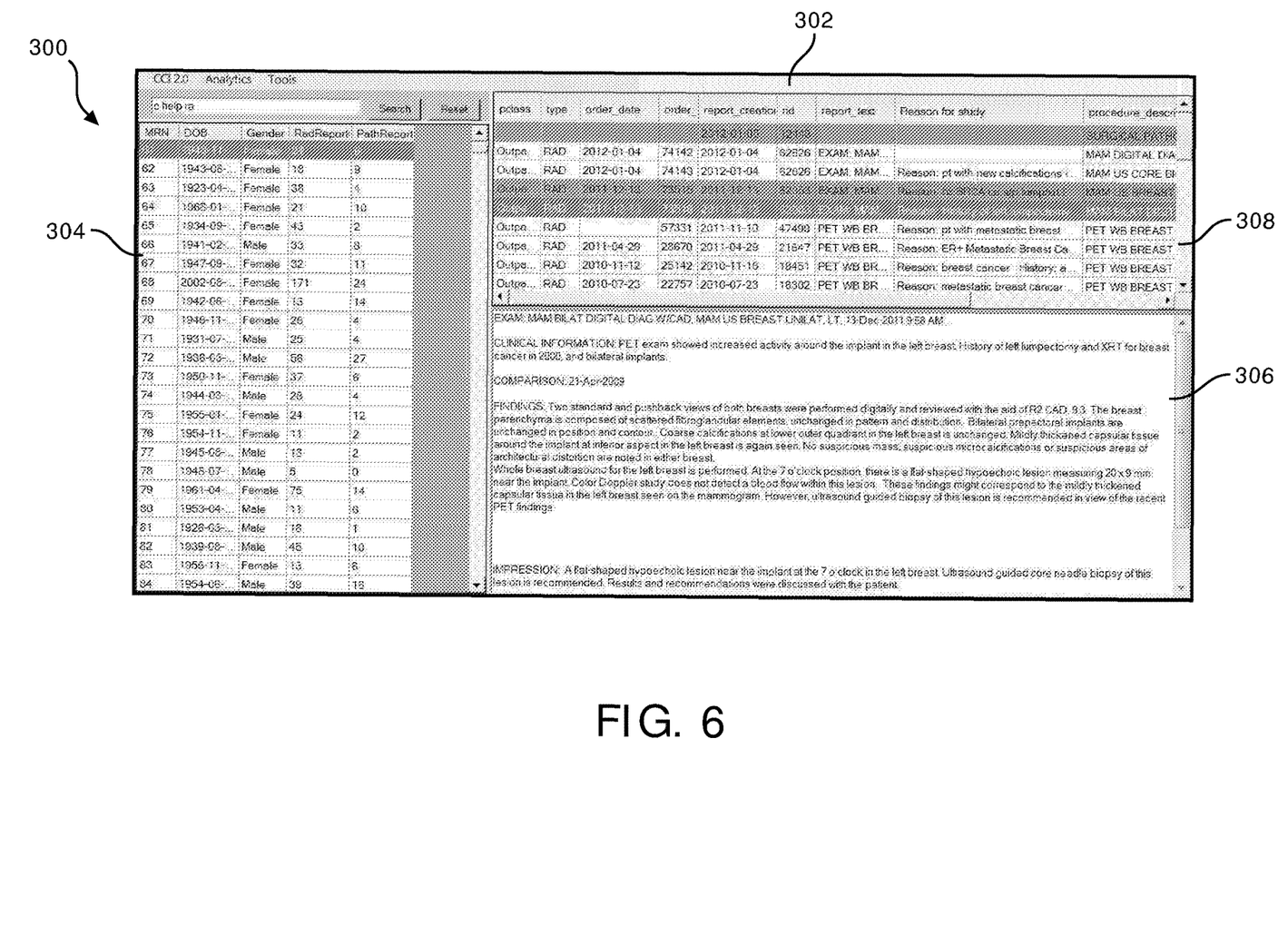
FIG. 6 illustrates another exemplary embodiment of a user interface generated by the clinical support system according to aspects of the present application.

With reference to FIG. 6, another exemplary embodiment of a user interface 300 generated by the clinical support system is illustrated. The user interface 300 includes a visualization of the correlation of studies for a particular patient. The user interface includes a list of clinical documents 302 corresponding to one or more patients 304 as well as a view of a clinical document selected by the user 306. The user interface 300 can highlight rows 308 of clinical documents which are correlated. The user interface 300 can be used in the routine clinical workflow by clinicians to review patient history and track quality assurance.

Figure 7:
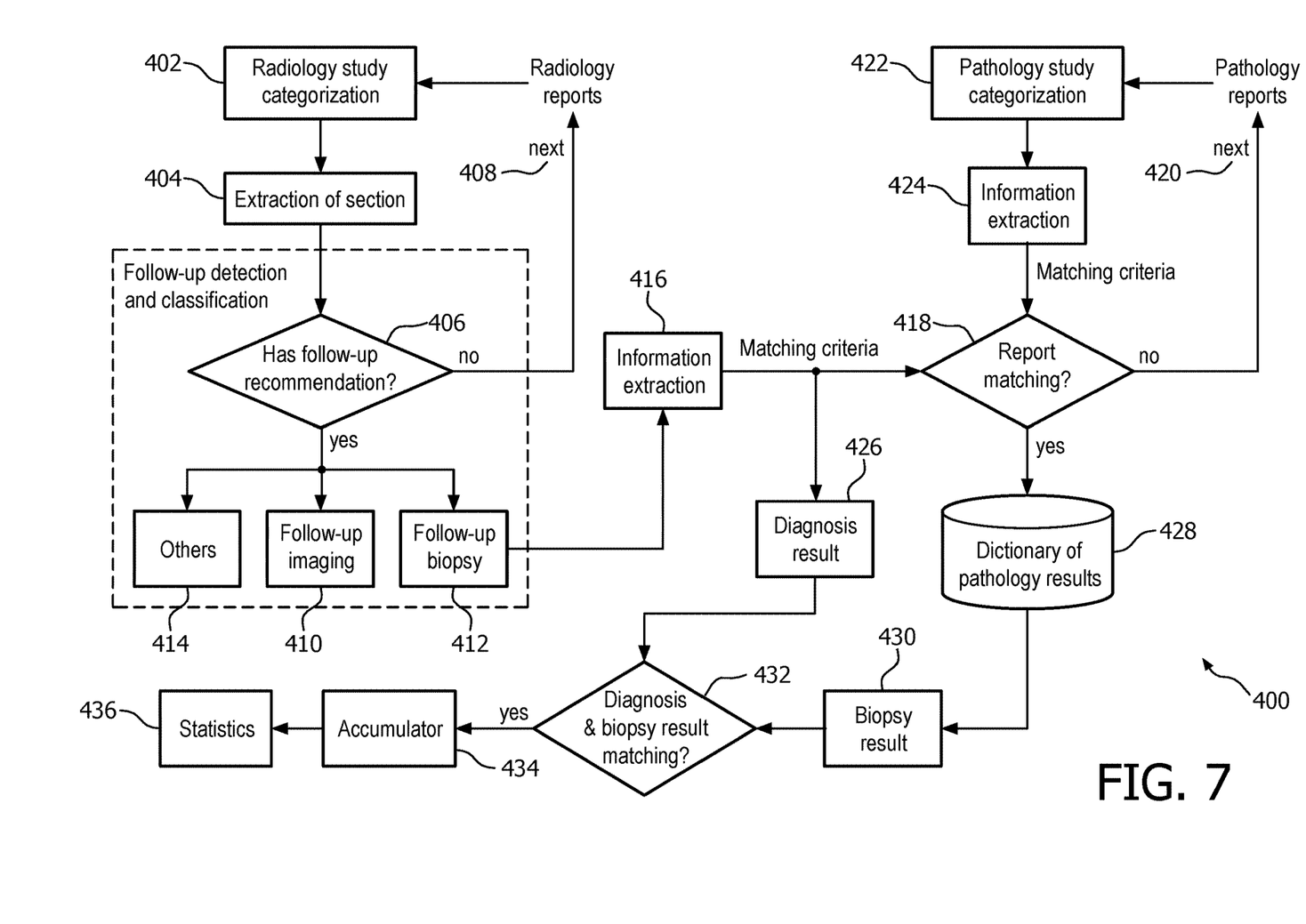
FIG. 7 illustrates an exemplary flowchart diagram of operation of a natural language processing engine according to aspects of the present application.

With reference to FIG. 7, an exemplary flowchart diagram 400 of operation of a natural language processing engine is illustrated. Although each of the blocks in the diagram is described sequentially in a logical order, it is not to be assumed that the system processes the described information in any particular order or arrangement. In a step 402, retrieved radiology reports are categorized. In a step 404, the sections of the radiology reports are extracted. In a step 406, it is determined if a follow-up has been recommended. If a follow-up has not been recommended, more radiology reports are retrieved in a step 408. If a follow-up has been recommended, the various follow-ups are performed including performing follow-up imaging in a step 410, performing a follow-up biopsy in a step 412, or performing other follow-ups in a step 414. If a follow-up biopsy is performed, information is extracted from the pathology report in a step 416. In a step 418, it is determined if the pathology reports matches. If the pathology report does not match, another pathology report is retrieved in a step 420. The retrieved pathology report is categorization in a step 422. In a step 424, information from the pathology report is extracted. In a step 418, it is determined if the retrieved pathology reports matches. In a step 426, the diagnosis results of the pathology reports are determined. In a step 428, a dictionary of pathology results is utilized to determine the biopsy results in a step 430. In a step 432, it is determined if the pathology diagnosis and biopsy results match. If the pathology diagnosis and biopsy results match, the results are provided to an accumulator in a step 434 and are then provided as statistics in a step 436.

Figure 8:
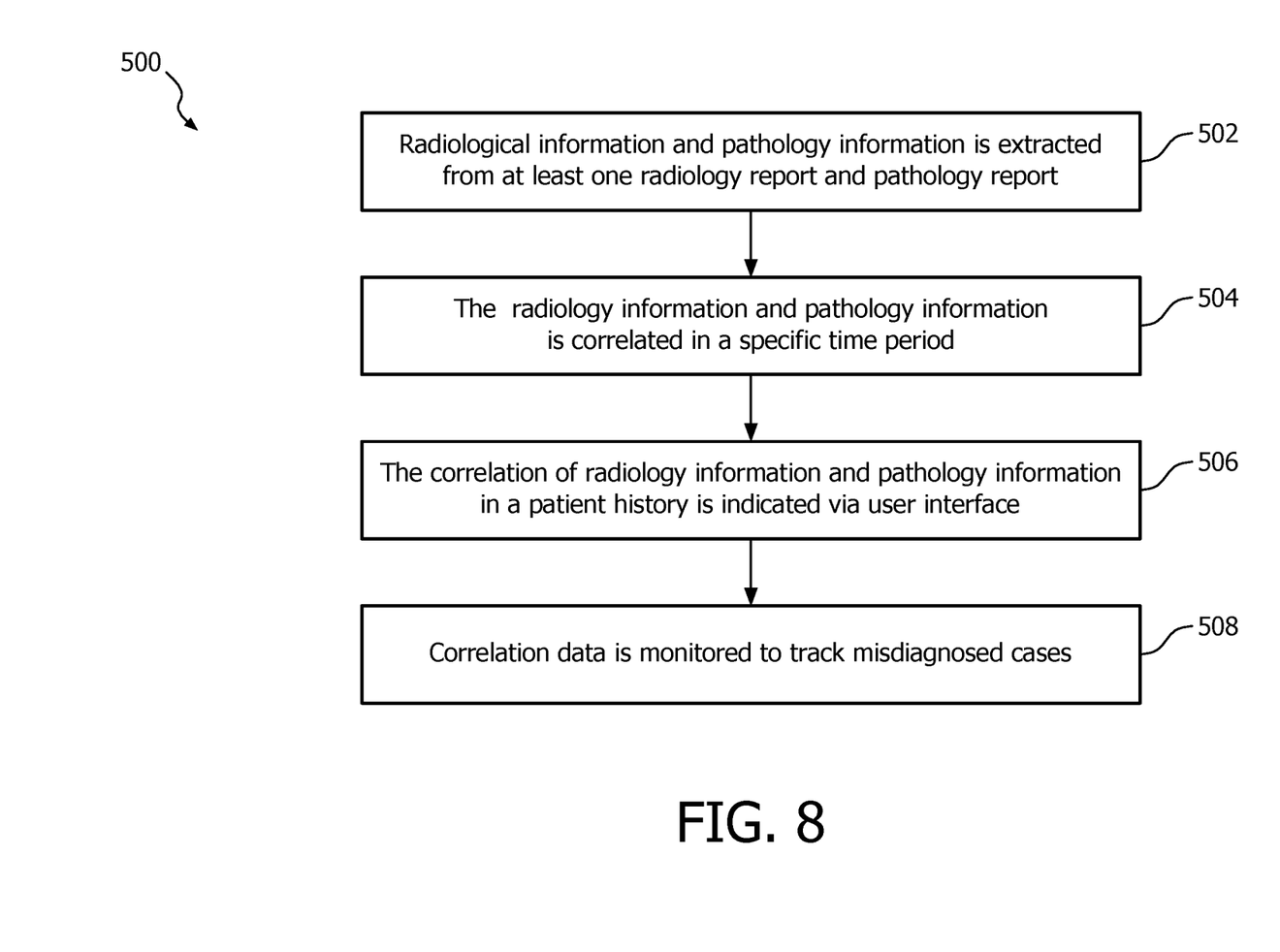
FIG. 8 illustrates a flowchart diagram of a method for correlating pathology and radiology reports according to aspects of the present application.

With reference to FIG. 8, a flowchart diagram 500 of a method for correlating pathology and radiology reports is illustrated. Although each of the blocks in the diagram is described sequentially in a logical order, it is not to be assumed that the system processes the described information in any particular order or arrangement. In a step 502, radiological information and pathology information is extracted from at least one radiology report and pathology report. In a step 504, the radiology information and pathology information is correlated in a specific time period. In a step 506, the correlation of radiology information and pathology information in a patient history is indicated via user interface. In a step 508, correlation data is monitored to track misdiagnosed cases.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), personal data assistant (PDA), cellular smartphones, mobile watches, computing glass, and similar body worn, implanted or carried mobile gear; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A system for correlating patient radiology and pathology reports to track discordance among radiology and pathology diagnoses, the system comprising instructions that, in response to execution of the instructions by one or more processors, cause the one or more processors to:
    perform natural language processing on clinical documents to extract radiology information and pathology information by identifying one or more predefined radiology study terms in radiology documents and one or more predefined pathology report terms in pathology documents, wherein the natural language processing extracts the radiology information and the pathology information according to the identification of the one or more predefined radiology study terms and the one or more predefined pathology report terms;
    correlate the radiology documents and pathology documents in a specific time period by identifying matching anatomy according to a shared clinical concept, the radiology documents and the pathology documents respectively including the extracted radiology information and the extracted pathology information;
    determine one or more misdiagnosis cases within the correlated radiology and pathology documents based on the extracted radiology and pathology information by identifying a mismatch of radiology diagnosis results with pathology results;
    based on the correlated radiology and pathology documents and the extracted radiology and pathology information, identify the one or more misdiagnosis cases to calculate key performance indicators for use in a visualization graphical user interface;
    generate data indicative of the visualization graphical user interface that indicates the correlation of radiology information and pathology information, wherein the visualization graphical user interface includes a visual scorecard that presents the calculated key performance indicators in spatial relation to accepted ranges of the key performance indicators; and
    based on the data, render, on a display, the visualization graphical user interface.

2. The system according to claim 1, wherein the natural language processing includes at least one of:
    determining whether a current radiology report suggests any follow-up procedures; and comparing a pathology report with a dictionary of known pathology result terms to find malignant diagnosis in the pathology report.

3. The system according to claim 1, further comprising instructions to provide more information in response to determining a misdiagnosis case.

4. The system according to claim 1, wherein one or more elements of the visual scorecard are selectable by a user to track more detail about each misdiagnosis.

5. The system according to claim 1, further comprising instructions to track cases of misdiagnosis using a data structure to store information of correlation allowing for tracking of true positive diagnosis and false positive diagnoses.

6. The system according to claim 5, wherein misdiagnosis information is tracked for a single radiologist over a specific period.

7. The system according to claim 5, wherein misdiagnosis information for a department of radiologists at a hospital is tracked over a specified period.

8. The system of claim 1, further comprising instructions to display to a user the correlations among radiology and pathology reports in a workflow for a user review of a patient history.

9. The system of claim 1, wherein the natural language processing includes:
extraction of key words from a free-text portion of a clinician report; and
input of the keywords to a classifier to classify the clinician report as either a pathology report or a radiology report.

10. A method for correlating patient radiology and pathology reports, the method implemented using one or more processors and comprising:
extracting radiology information and pathology information from at least one radiology report and at least one pathology report by identifying one or more predefined radiology study terms in radiology documents and one or more predefined pathology report terms in pathology documents according to the identification of the one or more predefined radiology study terms and the one or more predefined pathology report terms;
correlating the radiology documents and pathology documents in a specific time period by identifying matching anatomy according to a shared clinical concept, the radiology documents and the pathology documents respectively including the extracted radiology information and the extracted pathology information;
determining one or more misdiagnosis cases within the correlated radiology and pathology documents based on the extracted radiology and pathology information by identifying a mismatch of radiology diagnosis results with pathology results;
based on the correlated radiology and pathology documents and the extracted radiology and pathology information, identifying the one or more misdiagnosis cases to calculate key performance indicators for use in a visualization graphical user interface;
generate and store in memory data indicative of the visualization graphical user interface, wherein the visualization graphical user interface includes a visual scorecard that presents the calculated key performance indicators in spatial relation to accepted ranges of the key performance indicators; and
based on the data, render, on a display, the visualization graphical user interface.

11. The method according to claim 10, further including:
providing more information in response to determining a misdiagnosis case.

12. The method according to claim 10, wherein one or more elements of the visual scorecard are selectable by a user to track more detail about each misdiagnosis case.

13. The method according to claim 10, wherein the tracking includes using a data structure to store information of correlation allowing for tracking of true positive diagnosis and false positive diagnoses.

14. The method according to claim 10, further including:
displaying to a user correlations among radiology and pathology reports in a workflow for user review of a patient history.

15. The method of claim 10, further comprising:
extracting key words from a free-text portion of a clinician report; and
inputting the keywords to a classifier to classify the clinician report as either a pathology report or a radiology report.

16. A system for correlating patient radiology and pathology reports, the system comprising:
one or more processor programmed to:
extract radiology information and pathology information from at least one radiology report and at least one pathology report by identifying one or more predefined radiology study terms in radiology documents and one or more predefined pathology report terms in pathology documents according to the identification of the one or more predefined radiology study terms and the one or more predefined pathology report terms;
the radiology documents and pathology documents in a specific time period by identifying matching anatomy according to a shared clinical concept, the radiology documents and the pathology documents respectively including the extracted radiology information and the extracted pathology information;
based on the correlated radiology and pathology documents and the extracted radiology and pathology information, identify the one or more misdiagnosis cases to calculate key performance indicators for use in a visualization graphical user interface;
generate and store in memory data indicative of the visualization graphical user interface, wherein the visualization graphical user interface includes a visual scorecard that presents the calculated key performance indicators in spatial relation to accepted ranges of the key performance indicators; and
based on the data, render, on a display, the visualization graphical user interface.

17. The system according to claim 16, wherein the one or more processors are further programmed to:
provide more information in response to determining a misdiagnosis case.

18. The system according to claim 16, wherein the one or more processors are further programmed to track clinical outcomes of radiologists.

19. The system according to claim 18, wherein one or more elements of the visual scorecard are selectable by the user to track more detail about each misdiagnosis.

20. The system according to claim 18, wherein the one or more processors are further programmed to:
track cases of misdiagnosis using a data structure to store information of correlation allowing for tracking of true positive diagnosis and false positive diagnoses.

21. The system according to claim 16, wherein the one or more processors are further programmed to:
   determine whether information items in the at least one radiology report or the at least one pathology report refer to similar criteria.

22. The system of claim 16, wherein the one or more processors are further programmed to:
   extract of key words from a free-text portion of a clinician report; and
input of the keywords to a classifier to classify the clinician report as either a pathology report or a radiology report.

\* \* \* \* \*